US 6,180,131 B1

(12) United States Patent
Sunvold et al.

(10) Patent No.: US 6,180,131 B1
(45) Date of Patent: Jan. 30, 2001

(54) PROCESS FOR IMPROVING GLUCOSE METABOLISM, SATIETY, AND NUTRIENT ABSORPTION IN COMPANION ANIMALS

(75) Inventors: Gregory D. Sunvold, Eaton; Michael G. Hayek, Dayton, both of OH (US)

(73) Assignee: The Iams Company, Dayton, OH (US)

( * ) Notice: Under 35 U.S.C. 154(b), the term of this patent shall be extended for 0 days.

(21) Appl. No.: 09/055,790

(22) Filed: Apr. 6, 1998

Related U.S. Application Data

(60) Provisional application No. 60/042,957, filed on Apr. 7, 1997.

(51) Int. Cl.$^7$ ..................................................... A23K 1/17
(52) U.S. Cl. ......................... 424/442; 514/54; 514/777; 514/779; 514/780; 514/782; 426/2; 426/635
(58) Field of Search .......................... 424/442, 484–488; 514/22, 54, 777, 779, 780, 782; 426/2, 71, 636, 639, 640

(56) References Cited

U.S. PATENT DOCUMENTS 5,616,569 4/1997 Reinhart .................................. 426/2
5,776,524 * 7/1998 Reinhart .................................. 426/2

OTHER PUBLICATIONS

M.D. Howard et al., "Effect of Fermantable Fiber Consumption by the Dog on Nitrogen Balance and Fecal Microbial Nitrogen Excretion", FASEB J. (1996) 10:A257.

G.D. Sunvold et al., "Dietary Fiber for Dogs: IV. In Vitro Fermentation of Selected Fiber Sources by Dog Fecal Inoculum and In Vivo Digestion and Metabolism of Fiber–Supplemented Diets", J. Animal Sci. (1995) 73:1099–1109.

S.P. Massimino et al. "Fermentable dietary fiber improves glucose tolerance but not immune function in dogs" FASEB Journal, vol. 11, No. 3, 1997, Bethesda, Maryland US, p. A650, XP002072421.

R.A. Reimer et al., Dietary fiber modulates intestinal proglucagon messenger ribonucleic acid and postprandial secretion of glucagon–like peptide–1 and insulin in rats, Endocrinology, vol. 137, 1996, pp. 3948–3956, XP002072422.

H.E. Muir et al., "Nutrient digestion by ileal cannulated dogs as affected by dietary fibers with various fermentation characteristics", Journal of Animal Science, vol. 74, No. 7, 1996, pp. 1641–1648.

R. W. Nelson et al; "Effects of dietary fiber supplementation on glycemic control in dogs with alloxan–Induced diabetes mellitus", American Journal of Veterinary Research, vol. 52, No. 2, 1991, pp. 2060–2066.

R.V. Sharma et al; "Effect of pectin on carbohydrate and fat metabolism" Indian Journal of Medical Research, vol. 76, 1982, pp. 771–775, XP–002072420.

M. Dietz et al., "Influence of a blend of fructo–oligosaccharides and sugar beet fiber on nutrient digestibility and plasma metabolite concentrations in healthy Beagles" American Journal of Veterinary Research, vol. 58, No. 11, 1997, pp. 1238–1242, XP–002072352.

(List continued on next page.)

Primary Examiner—Neil S. Levy
(74) Attorney, Agent, or Firm—Killworth, Gottman, Hagan & Schaeff, L.L.P.

(57) ABSTRACT

A process for feeding an animal a diet which alters the function and morphology of the gastrointestinal tract (GIT), a large lymphoid organ in the animal and which improves glucose metabolism, satiety, and nutrient absorption. The process involves feeding a companion animal such as, for example, a dog or cat a diet of a pet food composition containing fermentable fibers which have an organic matter disappearance (OMD) of 15 to 60 percent when fermented by fecal bacteria for a 24 hour period, the fibers being present in amounts from about 1 to 11 weight percent of supplemental total dietary fiber. The animal is maintained on the diet for a sufficient period of time to allow the fermentable fibers to ferment in the GIT of the animal.

13 Claims, 8 Drawing Sheets

OTHER PUBLICATIONS

C. Stock–Damage et al., "Effect of dietary fiber supplementation on the secretory function of the exocrine pancreas in the dog", American Journal of Clinical Nutr., vol. 36, No. 6, 1983 pp. 843–848.

Willart M D et al., Effects of Dietary Supplementation of Fructo–Olgosaccharides On Small Intestinal Bacterial Overgrowth in Dogs:, Amer. Journ. of Veter. Research, vol. 55, May 1994, pp. 654–659.

* cited by examiner

PROCESS FOR IMPROVING GLUCOSE METABOLISM, SATIETY, AND NUTRIENT ABSORPTION IN COMPANION ANIMALS

CROSS REFERENCE TO RELATED APPLICATION

This patent application claims the benefit of U.S. Provisional Patent Application Ser. No. 60/042,957, filed Apr. 7, 1997.

BACKGROUND OF THE INVENTION

This invention relates to a process involving the use of a pet food composition containing fermentable fibers to improve glucose metabolism, satiety, and nutrient absorption in companion animals such as, for example, dogs and cats.

Recent research has suggested that dietary fiber is important for its fermentation properties in the large intestine of dogs and cats. For example, Reinhart, U.S. Pat. No. 5,616,569, describes the addition of fermentable dietary fiber to a pet food composition for the purpose of maintaining normal gastrointestinal function and ameliorating chronic diarrhea in animals. Howard et al, FASEB J. (1996) 10:A257, teach that fermentable fiber consumption by dogs can result in the partition of waste nitrogen from the urine to the feces, increasing nitrogen excretion through the feces of the animal. Sunvold et al, J. Anim. Sci. (1995) 73:1099–1109, found that feeding moderately fermentable fibers to dogs could promote gastrointestinal tract health by optimizing short chain fatty acid (SCFA) production in the intestines of the animals.

Certain animals, such as dogs, as well as humans, sometimes suffer from diabetes or have an impaired ability to regulate blood sugar levels. There are many causes of diabetes. Where diabetes or impaired blood glucose regulation has been diagnosed, medication and diet for the animal should be closely controlled. Currently, diets having high concentrations of nonfermentable fibers are used to treat diabetes. However, these nonfermentable fiber-containing diets often impair nutrient absorption by the animal, resulting in undesirable effects on the animal's health and well being.

Certain animals also may have a tendency towards excess caloric intake which increases the risk of the animal developing diabetes or other chronic diseases. It would be desirable to be able to manage caloric intake through dietary means so that the animal would become sated after meals, but without excessive caloric intake.

Other animals may have difficulty in digesting and absorbing nutrients from their diets. For example, animals which exhibit exocrine pancreatic insufficiency (EPI), a condition in which there is an insufficient secretion of enzymes by the pancreas, struggle to digest nutrients normally, especially fats, in their diets. It would be desirable to be able to improve such animals' nutrient absorption capabilities. Thus, there remains a need for additional dietary measures which will improve glucose metabolism, satiety, and nutrient absorption in companion animals without the adverse effects of diets containing nonfermentable fibers.

SUMMARY OF THE INVENTION

The present invention meets that need by providing a process for feeding an animal a diet which alters the function and morphology of the gastrointestinal tract (GIT), a large lymphoid organ, in ways which are beneficial to the animal's health and well being. The process involves feeding a companion animal such as, for example, a dog or cat a diet of a pet food composition containing fermentable fibers which have an organic matter disappearance (OMD) of 15 to 60 percent when fermented by fecal bacteria for a 24 hour period, the fibers being present in amounts from about 1 to 11 weight percent of supplemental total dietary fiber. The animal is maintained on the diet for a sufficient period of time to allow the fermentable fibers to ferment in the GIT of the animal. This fermentation results in an upregulation in the secretion of GLP-1 which improves glucose homeostasis and promotes satiety in the animal. The diet also enhances the absorption of nutrients by the animal by increasing the transport of D-glucose and lauric acid which are indicators of carbohydrate and fat absorption, respectively.

Preferably, the pet food composition contains from 2 to 10 weight percent of supplemental total dietary fiber of fermentable fibers. More preferably, the pet food composition contains from 3 to 9 weight percent of supplemental total dietary fiber of fermentable fibers. Most preferably, the pet food composition contains from 4 to 7 weight percent of supplemental total dietary fiber of fermentable fibers.

Preferably, the fermentable fibers have an organic matter disappearance of 20 to 50 percent. More preferably, the fermentable fibers have an organic matter disappearance of 30 to 40 percent.

In addition, the fermentable fibers are preferably selected from the group consisting of beet pulp, gum arabic, gum talha (a form of gum arabic), psyllium, rice bran, carob bean gum, citrus pulp, pectin, fructooligosaccharides or inulin, mannanoligosaccharides and mixtures thereof. More preferably, the fermentable fibers are selected from the group consisting of beet pulp, gum arabic and fructooligosaccharides. Most preferably, the fermentable fibers are a blend of beet pulp, gum talha, and fructooligosaccharides. A preferred weight ratio of beet pulp to fructooligosaccharides in the fermentable fiber blend is from about 3:1 to 6:1, and most preferably 4:1. A preferred weight ratio of beet pulp to gum talha to fructooligosaccharide is 6:2:1.5.

Accordingly, it is a feature of the present invention to provide a pet food composition and process for altering the function and morphology of the gastrointestinal tract to improve glucose metabolism and enhance glucose homeostasis, improve satiety, and enhance nutrient absorption in an animal. This, and other features and advantages of the present invention, will become apparent from the following detailed description, the accompanying drawings, and the appended claims.

DETAILED DESCRIPTION OF THE PREFERRED EMBODIMENTS

Figure 1A:
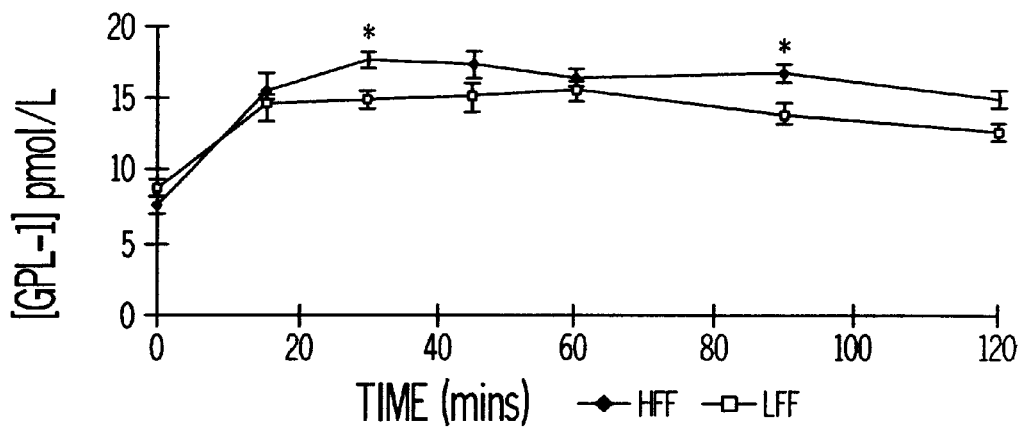
FIGS. 1A–1C illustrate the effect of fermentable fiber on plasma GLP-1(A), insulin (B), and glucose concentrations (C) after administration of an oral glucose tolerance test (OGTT), with significantly different time points ($p<0.05$) indicated by "*"

The present invention uses a pet food composition containing fermentable fibers to alter the function and morphology of the gastrointestinal tract of the animal. This provides a number of benefits to the animal. First, glucose metabolism is improved and glucose homeostasis is enhanced in the animal. While not wishing to be bound by any particular theory, it is believed that the improvement in glucose regulation in the animals results at least in part from the increased levels of insulinotropic gut hormones such as GLP-1 which are secreted in the gastrointestinal tract. GLP-1 is a potent insulinotropic hormone and potential antidiabetogenic agent. This upregulation of GLP-1 is believed to increase intestinal glucose transport capacity and improve glucose homeostasis in the animal. Increased levels of GLP-1 in the GIT of the animal also improve satiety in the animal and reduce the animal's tendency to overeat. These results are surprising in view of the prior art practice of using very high fiber concentration in animal diets, but using low fermentablility fibers such as cellulose to attempt to accomplish this result.

Further, the presence of fermentable fibers in the diet increases the transport of D-glucose and lauric acid in the jejunum (mid portion) of the small intestine. D-glucose and lauric acid are indicators of carbohydrate and fat absorption, respectively, in an animal. Thus, healthy animals will benefit from the process of the present invention which improves nutrient absorption. However, animals which are suffering from certain disease states such as exocrine pancreatic insufficiency (EPI) will benefit even more. EPI results from insufficient secretion of enzymes by the pancreas, with such enzymes being needed by the animal for normal nutrient digestion. Animals with EPI struggle to digest dietary nutrients, especially fats. Animals with EPI which are fed the pet food composition of this invention will benefit by an improved ability to absorb dietary nutrients.

The present invention uses a pet food composition containing fermentable fibers which display certain organic matter disappearance percentages. The fermentable fibers used in the present invention have an organic matter disappearance (OMD) of from about 15 to 60 percent when fermented by fecal bacteria in vitro for a 24 hour period. That is, from about 15 to 60 percent of the total organic matter originally present is fermented and converted by the fecal bacteria. The organic matter disappearance of the fibers is preferably 20 to 50 percent, and most preferably is 30 to 40 percent.

Thus, in vitro OMD percentage may be calculated as follows:

$$\{1-[(OM\ residue-OM\ blank)/OM\ initial]\} \times 100,$$

where OM residue is the organic matter recovered after 24 hours of fermentation, OM blank is the organic matter recovered in corresponding blank tubes (i.e., tubes containing medium and diluted feces, but no substrate), and OM initial is that organic matter placed into the tube prior to fermentation. Additional details of the procedure are found in Sunvold et al, J. Anim. Sci. 1995, vol. 73:1099–1109.

The pet food composition can be any suitable pet food formula which also provides adequate nutrition for the animal. For example, a typical canine diet for use in the present invention may contain about 30% crude protein, about 20% fat, and about 10% total dietary fiber. However, no specific ratios or percentages of these or other nutrients are required.

Fermentable fibers which are useful in the present invention produce short chain fatty acids (SCFAs) within a range of from about 28 to about 85 mmol SCFA per 1000 Calories (kcals) of metabolizable energy (ME), and more preferably within a range of from about 42 to about 71 mmol SCFA per 1000 ME kcals. This equates to a composition which has a total fermentable fiber content which yields from about 100 to about 350 mmol SCFA/kg of diet.

Millimoles of SCFAs per 1000 metabolizable energy kilocalories are calculated by first calculating the total Calories of metabolizable energy (ME) in a given diet composition per kilogram of the composition. The number of grams per 1000 kcal ME may be derived from the first calculation. Then the grams, and thus millimoles, of the fermentable fiber components of the composition may be calculated.

The fermentable fiber of the present invention may be any fiber source which intestinal bacteria present in the animal can ferment to produce significant quantities of SCFAs. "Significant quantities" of SCFAs, for purposes of this invention, are amounts over 0.5 mmol of total SCFAs/gram of substrate in a 24 hour period. Preferred fibers include beet pulp, gum arabic (including gum talha), psyllium, rice bran, carob bean gum, citrus pulp, pectin, fructooligosaccharides or inulin, mannanoligosaccharides and mixtures of these fibers. More preferably, the fermentable fibers are selected from the group consisting of beet pulp, gum arabic and fructooligosaccharides. Most preferably, the fermentable fibers are a blend of beet pulp, gum talha, and fructooligosaccharides. A preferred weight ratio of beet pulp to fructooligosaccharides in the fermentable fiber blend is from about 3:1 to 6:1, and most preferably 4:1. A preferred weight ratio of beet pulp to gum talha to fructooligosaccharide is 6:2:1.5.

The fermentable fibers are used in the pet food composition in amounts from 1 to 11 weight percent of supplemental total dietary fiber, preferably from 2 to 10 weight percent, and most preferably from 3 to 7 weight percent.

A definition of "supplemental total dietary fiber" first requires an explanation of "total dietary fiber". "Total dietary fiber" is defined as the residue of plant food which is resistant to hydrolysis by animal digestive enzymes. The main components of total dietary fiber are cellulose, hemicellulose, pectin, lignin and gums (as opposed to "crude fiber", which only contains some forms of cellulose and lignin). "Supplemental total dietary fiber" is that dietary fiber which is added to a food product above and beyond any dietary fiber naturally present in other components of the food product. Also, a "fiber source" is considered such when it consists predominantly of fiber.

In order that the invention may be more readily understood, reference is made to the following examples which are intended to illustrate the invention, but not limit the scope thereof.

EXAMPLE 1

Diets, see Table 1, were formulated to be isonitrogenous and isoenergetic and to provide approximately 19.5 MJ/kg diet with 35% of the energy from carbohydrate, 30% from fat and 35% from protein. The low fermentable fiber (LFF) diet contained wood cellulose as the fiber source and the high fermentable fiber diet (HFF) diet contained a blend of more fermentable plant fibers (beet pulp, Michigan Sugar, Saginaw, Mich.; gum arabic, TIC Gums, Belcamp, Md.; fructooligosaccharides (FOS), Golden Technologies Corporation, Golden, Colo.). The ratio of beet pulp to gum arabic to FOS was about 6:2:1.5. The ratio of beet pulp to FOS was about 4:1.

Adult mongrel dogs (n=16) were utilized. Upon arrival, animals were acclimatized for 7 days and fed a nutritionally complete diet (Can-Pro, Beaumont, Ala.). All dogs were weighed daily and individually fed to meet energy requirements using the formula: Energy intake (MJ)=0.553×kg (body weight)$^{0.67}$. Food was offered once daily between 0900–1000 hours and water was available ad libitum. A crossover experimental design was used whereby dogs were randomly assigned to receive the HFF or LFF diet for 14 days, followed by the alternate diet for an additional 14 days. Because the 16 dogs could not be accommodated at one time, the dogs were paired throughout the experiment.

Oral Glucose Tolerance Test. Food was removed at 1600 hours on days 13 and 27. At 0845–0900 hours on days 14 and 28, the dogs were loosely restrained in a table sling and an oral glucose tolerance test (OGTT) was conducted using 70% (w/w) dextrose to provide 2 g glucose/kg body weight. Peripheral blood was sampled at 0, 15, 30, 45, 60, 90 and 120 min via an Insyte-W 20GA 2" catheter (Becton-Dickinson Vascular Access, Sandy, Utah) placed in the saphenous vein.

Peripheral blood samples. Blood samples for general chemistry screen and complete blood counts (2 ml) were placed into 3 ml heparinized Vacutainer tubes (trademark, Becton-Dickinson, Sunnyvale, Calif.) and stored on ice until analysis. Hematological analyses were conducted using a Coulter STKS instrument (Courter Electronics Inc., Hialeah, Fla.) and manual differential counts were performed. Blood samples for insulin and GLP-1 analysis were collected into 10 ml EDTA heparinized Vacutainer tubes with aprotinin (500 KIU/ml blood, Sigma Chemicals, St. Louis, Mo.) and stored at −70° C. (GLP-l) or −35° C. (insulin). Blood samples for serum glucose determinations were placed in 250 μL microcentrifuge tubes and centrifuged at 2900×g for 10 min at room temperature. The serum was removed by pipes and stored at −35° C.

Intestinal samples. On day 28, the dogs were anesthetized by intravenous injection of somnitol (MTC Pharmaceuticals, Cambridge, ON) using 1 ml/2.27 kg body weight via the saphenous catheter subsequent to the OGTT. Intestinal samples were taken for northern blot analysis and immediately placed in liquid nitrogen. Jejunal and ileal samples for nutrient uptake assays were placed in ice-cold saline and assays were performed within 30 min of sampling. Jejunal and ileal segments were scraped to obtain mucosal samples for western blot analyses. Histological samples were placed directly into formalin and slides were prepared.

Glucose. Serum glucose was determined using the Sigma Diagnostics Glucose (Trinder) Reagent for the enzymatic determination of glucose at 505 nm (Cat #315–100, Sigma Chemical, St. Louis Mo.).

Insulin. Serum insulin concentrations were determined using the Coat-A-Count® l$^{125}$ diagnostic radioimmunoassay (Cat # TKIN1, Diagnostics Products Corporation, Los Angeles, Calif.).

Plasma GLP-1(7-36)NH$_2$ Extraction. GLP-1 immunoreactive peptides were extracted as from 2.5 ml of plasma as described by Reimer and McBurney, Endocrinol. 137:3948–3956 (1996). A SEP-COLUMN was used containing 200 mg of C$_{18}$ (Cat # RIK-SEPCOL 1, Peninsula-Laboratories, Belmont, Calif.) with Buffer A (0.1% trifluoroacetic acid (Cat # RIK-BA-1) and Buffer B (60% acetonitrile (Cat # RIK-BB 1) as elusion solvents. Samples were lyophilized overnight using a Speed-Vac (trademark, Savant Inc., Midland, Mich.) and stored at −70° C.

Intestinal GLP-1(7-36)NH$_2$ Extraction. Extraction of GLP-1(7-36)NH$_2$ from intestinal segments has been described by Xioyan, PhD thesis, University of British Columbia, Vancouver (1996) and was carried out with modifications. 400–500 mg of each segment (jejunum, ileum and colon) was added to a 12×75 mm Simport polypropylene tube (Fischer Scientific, Edmonton, AB) with 0.5 ml 2M acetic acid and boiled for 1 hour. Tubes were centrifuged at 4500×g for 10 min, the supernatant collected, transferred to a fresh tube and neutralized with 1N NaOH. For RIA purposes, the sample of supernatant was diluted 1:10 with RIA buffer (100 mM Tris, 50 mM NaCl, 200 mM Na$_2$-EDTA, 0.2 g/L Na azide, pH 8.5) to give a final sample volume of 100 μL.

GLP-1(7-36)NH$_2$ Radioimmunoassay. Concentrations of GLP-1(7-36)NH$_2$ were measured using a competitive binding radioimmunoassay described by Xiaoyan (1996) with modifications. The lyophilized plasma samples were reconstituted in 250 μL of RIA assay buffer (100 mM Tris, 50 mM NaCl, 20 mM Na$_2$-EDTA, 0.2 g/L Na azide, pH 8.5). Polypropylene tubes (12 mm×75 mm) were used for controls, standards and samples and the entire procedure was carried out on ice. GLP-1 (7-36 NH$_2$) standards (Peninsula Laboratories, Belmont, Calif.) made from serial dilutions, ranged from 4000 pg/ml to 15 pg/ml. Tubes were mixed and incubated 24 hours at 4° C. Following incubation, 15 Bq of $^{125}$l-GLP-1(736)NH$_2$ tracer was added to the tubes, the tubes were mixed by vortexing and incubated for 48 hours at 4° C. A dextran-charcoal suspension (4 g/L dextran T70, 80 g/L charcoal in assay buffer) was added to all tubes (100 μL) except TC tubes. Tubes were mixed by vortexing and left on ice for 15 min, centrifuged at 2200×g for 30 min and 600 μL of supernatant was transferred to new tubes which were counted using a Cobra™ Auto-Gamma counter (Packard Instrument Company, Downers Grove, Ill.).

GLP-1 (7-36)NH$_2$ Iodination. GLP-1 (7-36 NH$_2$) was iodinated using the chloramine-T method as described by Xiaoyan (1996). The cartridge was primed by allowing 10 ml acetonitrile with 0.1% trifluoroacetic acid (TFA) followed by 10 ml of ddH$_2$O with 0.1% TFA to flow through. The cartridge was dried by pushing 10 ml air through the cartridge with a syringe. The iodination was carried out by first dissolving 30–40 μg of GLP-1 in 30–40 μL of ddH$_2$O, then 10 μL was transferred to a fresh eppendorf tube. To this, 10 μL 0.5 M PO$_4$ (pH 7.0) was added followed by 0.5 m Ci$^{125}$l. Chloramine-T (10 μL) was added and the tube was tapped for exactly 30 seconds. Sodium metabisulfite (5 mg/ml) was added, followed by 1 ml of 0.1% TFA which was then transferred to the primed column. Gentle pressure was applied to the column using a 10 cc syringe. Acetonitrile with 0.1% TFA was used as the elutant to acquire 5 fractions. Acetonitrile (5 ml, 10%+0.1% TFA) and acetonitrile (5 ml, 20%+0.1% TFA) are the first 2 elutants used in that order and the fractions were collected into 14 mL round bottom tubes. Then 30% acetonitrile (1 ml+0.1 % TFA, 4 times), 38% acetonitrile (1 ml+0.1% TFA, once) and 40% acetonitrile ( 1 ml+0.1% TFA 5 times) were used as the next elutants in that order and the fractions were collected in small polypropylene tubes. Each eluted fraction was mixed well and 10 µL from each fraction was counted using a Cobra™ Auto-Gamma counter. The label was usually eluted in fraction 1, 2 and/or 3 of the 40% acetonitrile. Fractions containing the labeled GLP-1(7-36)$NH_2$ were pooled and stored at −35° C. The $^{125}$IGLP-1 (7-36)$NH_2$ has a storage life of approximately 2 weeks.

Isolation of Total RNA. Total RNA was isolated from each intestinal segment using Trizol™ (Gibco BRL, Burlington, ON) according to the protocol provided by the manufacturer. 400–500 mg of tissue was ground in a pre-chilled sterile mortar with pestle. The ground tissue (200 mg in duplicate) was weighed and transferred in duplicate to polypropylene tubes (12 mm×75 mm), 2 ml of Trizol™ solution was added and samples were homogenized with a Polytron homogenizer for 30 seconds at setting 10. The homogenized sample was transferred to a 14 ml sterile polypropylene Falcon™ tube and incubated for 5 min at room temperature. To each sample, 400 µL of chloroform was added, and the tubes vigorously hand shaken for 15 sec and incubated for another 2–5 min at room temperature. Next, samples were centrifuged at 12,000×g for 15 min at 4° C. The aqueous phase was transferred to a fresh eppendorf tube, and 1 ml isopropanol was added to the tubes. The tubes were then vortexed, and the RNA precipitated overnight at −20° C. Samples were centrifuged at 10,000–12,000×g for 10 min at 4° C., the supernatant was removed, and the pellet was washed two times with 75% ethanol (at least 1 ml). The sample was mixed by vortexing and pelleted by centrifuging at 7,500×g for 10 min at 4° C. The RNA pellet was briefly allowed to air dry (no more than 10 min). The RNA pellet was dissolved in RNAse free water (50–100 µL per 100 mg of tissue) by gentle vortexing, incubated for 5–10 min at 55–60° C. and stored at 70° C. Quantity and purity of RNA were determined by ultraviolet spectrophotometry at 260, 280 and 230nm.

Northern Blot Analysis. Messenger RNA was measured by northern blot analysis as described by Zhao et al, Intern. J. Bioch. 25:1897–1903 (1993). Aliquots of 15 µg total RNA were each dissolved in 10 µL loading gel buffer (50% deionized formamide (vol/vol), 2M formaldehyde, 1.3% glycerol (vol/vol), 0.02M morpholinopropanesulphonic acid (MOPS), 5 mM sodium acetate, 1 mM EDTA and 0.1% bromophenol blue (wt/vol)). The dissolved RNA aliquots were boiled for 2 min to denature the RNA, and then loaded onto a 1% agarose (wt/vol) gel containing (0.66M) formaldehyde RNA was fractionated according to size by electrophoresis in the presence of a recirculating running buffer containing 0.02M MOPS, 5 mM sodium acetate and 1 mM EDTA (5 hours at 100V). After electrophoresis, the gels were soaked in two changes of 10×standard saline citrate (SSC) (1.5M NaCl, 0.15M trisodium citrate, pH 7.0) and blotted onto a zeta-probe GT Genomi tested blotting membrane (BioRad, Mississauga, ON). The RNA was fixed onto membranes by baking in vacuum at 80° C. for 2 hours. Prior to hybridization with [$^{32}$P] CTP-labeled riboprobe, each membrane was prehybridized for 2 hours at 50° C. in 20 ml of prehybridization buffer (deionized formamide (60% vol/vol), 20×SSPE (5% vol/vol), 10% blotto (5% vol/vol), 20% SDS (5% vol/vol), and 10 mg/ml sheared salmon DNA (denatured by boiling in a hot water bath for 10 min, 5% vol/vol)). Hybridization was carried out for 12–16 hours at 50° C. in an identical volume of fresh hybridization solution (deionized formamide (55% vol/vol), 20×SSPE (5% vol/vol), 10% blotto (5% vol/vol), 20% SDS (5% vol/vol), and 10 mg/ml sheared salmon DNA (2.5% vol/vol mixed with an equal part of deionized formamide. To this, 16.7 KBq (1×10$^6$ cpm) of labeled riboprobe was added and pre-warmed in a 70° C. water bath for 5 min before being added to the pre-warmed hybridization solution. The membranes were washed with 2×SSC at room temperature for 5 min and then in 2×SSC/0.1% SDS for either 10 min (GLUT2) or 15 min (proglucagon, SGLT-1). The membranes were transferred to a bath of 0.2×SSC/1% SDS as follows: proglucagon (70° C. for 10 min), SGLT-1 (70° C. for 20 mins), and GLUT2 (60° C. for 2–3 min). Lastly, the membranes were washed in 0.2×SSC at room temperature for 2–3 min. Membranes were heat sealed in plastic bags and exposed to Kodak XRA5 film (Eastman Kodak, Rochester, N.Y.) at −70° C. using an intensifying screen (Dupont Canada, Mississauga, ON). For statistical analysis, the signals were quantified using laser densitometry (Model GS-670 Imaging Densitometer, Bio-Rad Laboratories (Canada) LTD., Mississauga, ON). The 28S and 18S ribosomal bands were quantified from negatives of photographs of the membranes. These bands were used to confirm the integrity of the RNA and compensate for minor loading discrepancies.

Riboprobes. A 3.8 kb radiolabeled GLUT2 antisense riboprobe was generated from Xba I-linearized plasmid DNA [pGEM4Z-HTL-3] and T7 polymerase. The 350 kb proglucagon sense riboprobe was generated from Rsa I-linearized plasmid DNA [pGEM4Z-HTL-3] and Sp6 polymerase. Lastly, the 2.1 kb SGLT-1 antisense riboprobe was generated from a 1.4 Kb fragment of lamb intestinal SGLT-1 clone (aa 207-664) (Wood et al, Bioch. Soc. Trans. 22:266s 1994).

BBM and BLM Isolation, Preparation and Enrichment. All procedures were performed on ice using previously described procedures (Maenz and Cheeseman, Biochem. Biophsy. Acta 860(2):277–285 (1986)). Approximately 5 gm of mucosal scrapings were added to 15 ml of membrane suspension solution, (MSS buffer, 125 mM/I sucrose, 1 mM/I Tris-HCL, 0.05 mM/L PMSF, pH 7.4) and homogenized with a Polytron homogenizer for 30 seconds at setting 8. Aliquots of this homogenate were then taken for enrichment assays. The samples were split into two 30 ml eppendorf tubes and 20 ml of MSS buffer added to each tube. Each tube was homogenized twice more at setting of 8 for 30 seconds. Samples were then centrifuged for 15 min at 2400×g, the supernatant was collected and centrifuged at 43,700×g for 20 min. The remaining pellet consisted of two fractions. The outer white fluffy layer comprised the basolateral membranes (BLM), and the inner dark brown pellet comprised the brush border membranes (BBM). BLM were gently resuspended in a small amount of MSS buffer and transferred to a 14 ml eppendorf tube. BBM were resuspended in MSS buffer and samples from the same animal were pooled into 1 tube and made up in 20 ml of MSS buffer. BBM were then centrifuged for 20 min at 43,700×g. Again the fluffy white pellet was gently resuspended with MSS buffer and added to the 14 ml eppendorf tube and the dark pellet was resuspended in exactly 30 ml of MSS buffer. Isolated BLM were homogenized for 15 seconds on setting 8. Each sample was loaded on 25 ml 20% Percoll® and centrifuged for 30 min at 46,000×g. The resulting fluffy band in the Percoll collected and transferred to 25 mm×89 mm polycarbonate ultracentrifuge tubes (Beckman Instruments Inc., Palo Alto, Calif.), then brought up to volume (approximately 38 ml) with MSS buffer, and centrifuged at 115,000×g for 30 min. The membrane layer was removed, diluted with 20 ml of MSS buffer, and homogenized for 15 seconds with the Polytron® at setting 8. $CaCl_2$ (1M, 100 $\mu$L) was added and stirred gently on ice for 10 min. Samples were centrifuged for 10 min at 7700×g, the pellet resuspended in 20 ml MSS buffer, and homogenized for 15 seconds at setting 8. Samples were centrifuged another 20 min at 46,000×g and the pellet was resuspended in 1 ml MSS buffer. Aliquots were then taken for marker enrichment assays. BBM samples were homogenized for 15 seconds with the Polytron at setting 8 and centrifuged for 10 min at 1,900×g. The supernatants were transferred to new tubes and centrifuged another 15 min at 14,600×g. Again, the supernatants were transferred to new tubes containing 300 $\mu$L of 1 M $CaCl_2$, and stirred gently on ice for 20 min. Samples were centrifuged for 30 min at 3,000×g, the supernatant was collected, and centrifuged another 30 min at 46,000×g. The pellet was resuspended in 1 ml of dd$H_2$O and aliquots were taken for enrichment assays. The enrichment assay described by Esmann, Methods in Enzymology 156:72–79 (1988) was used for the BLM enzyme $Na^+K^+$-ATPase. Total ATPase activity was assayed by incubating mucosal homogenates and membrane preparations in the presence of ATP and $Mg^{2+}$, and measuring the liberated inorganic phosphate using the classic molybdenum reaction. Ouabain-insensitive ATPase activity was assayed as described above in the presence of ouabain. $Na^+k^+$-ATPase activity is ouabain sensitive, therefore the difference between total and ouabain-insensitive ATPase activity is the $Na^+K^+$-ATPase activity. Results are expressed as percent-fold enrichment. The enrichment assay for the BBM enzyme alkaline phosphatase was measured using the alkaline phosphatase kit from Sigma (Cat #245-10, Sigma Diagnostics, St. Louis, Mo.). The procedure is based on the hydrolysis of p-nitrophenyl phosphate to p-nitrophenol and inorganic phosphate by alkaline phosphatase. The p-nitrophenol formed is yellow in color and shows a maximum absorbance at 405 nm.

Western Blot Analysis. The western blot analysis protocol described by Tappenden, PhD Thesis, University of Alberta, Edmonton, Canada (1997) was used for the quantification of BBM and BLM glucose transporters. BLM (60 $\mu$g isolated protein) samples were diluted 1:4 with 1×sample buffer (0.5M Tris-HCl pH 6.8 (13.2% vol/vol), glycerol (10.5% vol/vol), 0.05% (w/vol) bromophenol blue and 10% SDS (0.21% w/vol)). BBM (60 $\mu$g isolated protein) samples were diluted 3:1 with 4×sample buffer (0.24M Tris-HCL, 40% glycerol, 8% vol/vol of 10% w/vol SDS, 0.5 mL bromophenol blue). BBM samples were boiled for 10 min, but not the BLM samples. The stacking gel (4.1M acrylamide/21 mM N'N-bis methylene-acryl (10.7% vol/vol), 0.5M Tris-HCL, pH 6.8 (0.24% vol/vol), 10% (w/vol) SDS (0.97% vol/vol), 10% APS w/v (4.86% vol/vol) and 0.4% TEMED (vol/vol)) was placed on top of the separating gel (4.1 M acrylamide/ 21 mM N'N-bis methylene-acryl (32.1% vol/vol), 1.5 M Tris-HCL, pH 8.8 (32.1% vol/vol), 10% (w/vol) SDS (1.3% vol/vol), 10% (w/vol) APS (0.66% vol/vol) and 0.16% (vol/vol) TEMED). Electrophoresis was carried out in running buffer (0.3% Tris (w/vol), 1.44% glycine (w/vol) and 0.1% SDS)) at 100–200 V for 1–2 hours until the dye front reached the end of the gel. Proteins were then transferred for 1.5–2 hours at 200 V onto a nitrocellulose membrane (MSI Laboratories, Houston, Tex.) using a transfer unit (BioRad, Mississauga, ON) with transfer buffer (Tris-base (0.189% w/vol), glycine (0.9% w/vol), methanol (20% vol/vol), SDS (0.02% w/vol)). Following the transfer, the membranes were placed immediately into TBST (1M Tris pH 7.5 (2% vol/ vol), NaCl (0.88% w/vol), 0.05% Tween-20 (0.05% vol/ vol)). Membranes were blocked in TBSTM (TBST with 5% (w/vol) powdered milk) for at least 1 hour with gentle agitation, and then incubated with primary antibodies to SGLT-1 (Cat # AB1352, Chernicon International Inc., Temecula, Calif.) at a dilution of 1:1000 or GLUT2 (Cat # AB1342) at a dilution of 1:500 overnight at 4° C. Membranes were washed 3×10 min in TBST with gentle agitation, and then incubated with the secondary antibody (anti-rabbit IgG HRP-conjugate, Signal Transduction, PDI Bioscience, Inc., Aurora, ON) at a dilution of 1:4000 for at least 2 hours with gentle agitation. Blots were covered completely with Supersignal CL-HRP™ (Cat #34080, Pierce, Rockford, Ill.) working solution and incubated for 5 min before being exposed to KODAK XRA5 film. Loading consistency and protein transfer was confirmed by staining the blots with Ponceau S (0.1% w/vol Ponceau S (BDH), 5% acetic acid). Statistical analysis was performed on the relative intensities of the bands. For statistical analysis, the signals were quantified using laser densitometry.

Measurement of Transport Kinetics. Transport kinetics were measured as described by Thomson and Rajotte, Am. J. Clin. Nutr. 38:394–403 (1983). A 12 cm segment of intestine was removed from each animal, opened along the mesenteric border and carefully washed with ice-cold saline to remove visible mucus and debris. Pieces of intestine (1 $cm^2$) were cut out and the tissue was mounted as flat sheets in incubation chambers containing oxygenated Kreb's bicarbonate buffer (pH 7.4) at 37° C. Tissue discs were preincubated in this buffer for 15 min to allow equilibration at this temperature. After preincubation, the chambers were transferred to beakers containing [$^3$H]insulin and various [$^{14}$C]-probe molecules in oxygenated Kreb's bicarbonate buffer (pH 7.4) at 37° C. The concentration of solutes was 4, 8, 16, 32 and 64 mM for D-glucose and D-fructose, 16 m for L-glucose, and 0.1 mM for lauric acid. The preincubation and incubation solutions were mixed using circular magnetic bars which were adjusted with a strobe light to achieve a stirring rate of 600 rpm and a low effective resistance of the intestinal unstirred water layer. The experiment was terminated by removing the chambers, quickly rinsing the tissue in cold saline for approximately 5 seconds and cutting the exposed mucosal tissue from the chamber with a circular steel punch. The tissue was dried overnight in an oven at 55° C. to determine the dry weight of the tissue and then saponified with 0.75 N NaOH. Scintillation fluid (Beckman Ready Solv HP, Toronto, ON) was added to the sample and radioactivity determined using an external standardization technique to correct for variable quenching of the two isotopes (Beckman Beta LS-5801, Beckman Instruments Inc, Mountain View, Calif.). The uptake of nutrients was expressed as nmol/100 mg dry tissue/ minute.

Villi Height and Crypt Depth Measurements. Intestinal segments were cut into sections. Intestinal villi height and crypt depths were measured under a light microscope using Northern Exposure Image Analysis software (Empix Imaging Inc., Mississauga, ON). A total of 10 recordings were made for each animal and each segment, with the average used for statistical analysis.

Statistical Analyses. All statistical analyses were performed using the Statistical Analysis System (SAS) statistical package (version 6.10, SAS Institute, Cary, N.C.). For proglucagon and SGLT-1 mRNA abundance, and SGLT-1 and GLUT2 transporter abundance, data was analyzed using the general linear models procedure (proc GLM) and significant differences were identified by one-way ANOVA. The model included diet, gel, period, pair and diet period. Both period and diet period were found to be non-significant and subsequently excluded. Villi height, crypt depth and intestinal GLP-1 concentrations were analyzed using proc GLM and the one-way ANOVA that included diet and pair. Again both period and diet period were non-significant and excluded from the model. Plasma AUC for GLP-1, insulin and glucose were analyzed using paired T-tests within proc GLM. Repeated measures ANOVA was used to analyze for differences between animal weights. The effect of period of feeding was tested but not significant (p>0.05). Intestinal transport rates for D-glucose, L-glucose, D-fructose and fatty acid 12 were analyzed using paired T-tests within proc GLM. Data presented are means±SEM. Significant differences were identified when p<0.05.

Effect of diet on body weight. Energy requirements were individually calculated and dietary portions were adjusted accordingly such that dog weights did not differ by experimental diet (23.4±1.8 kg, 22.9±1.8 kg, 23.5±1.8 kg for pre-experimental, HFF and LFF respectively) or by period (23.4±1.8 kg, 23.4±1.8 kg, 23.4±1.8 kg for pre-experimental [day 7], period 1 [day 21], and period 3 [day 35], respectively).

Figure 1B:
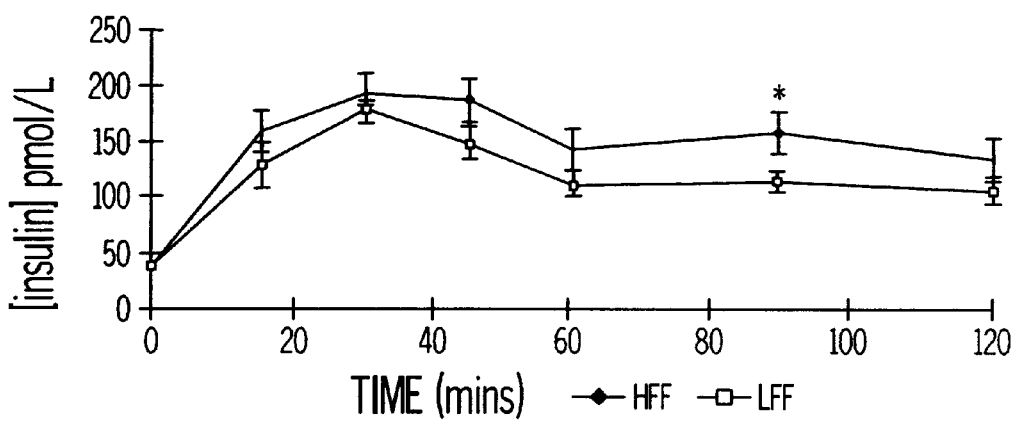
Figure 1C:
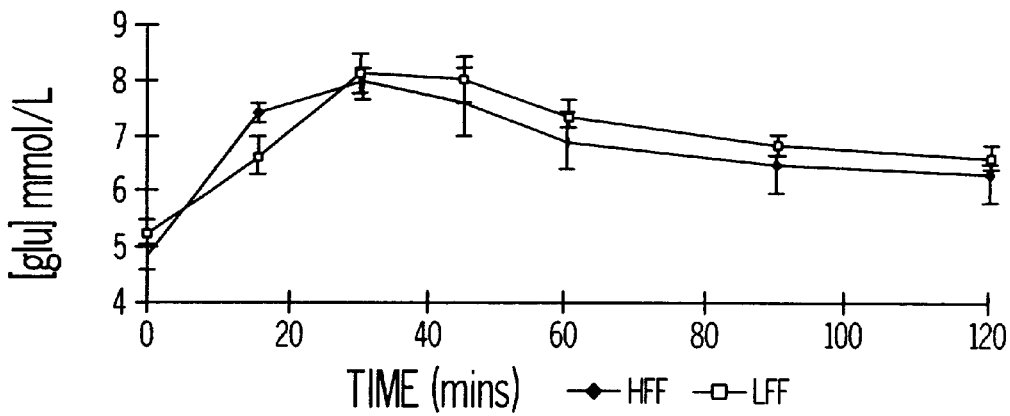
Figure 2A:
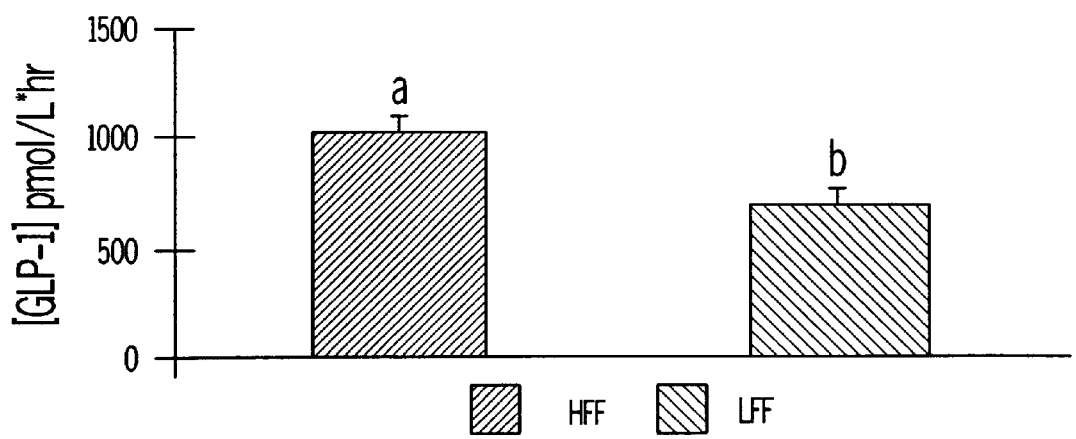
FIGS. 2A–2C illustrate the incremental area under the curve for plasma GLP-1(A), insulin (B), and glucose (C) after administration of an oral glucose tolerance test (OGTT)
Figure 2B:
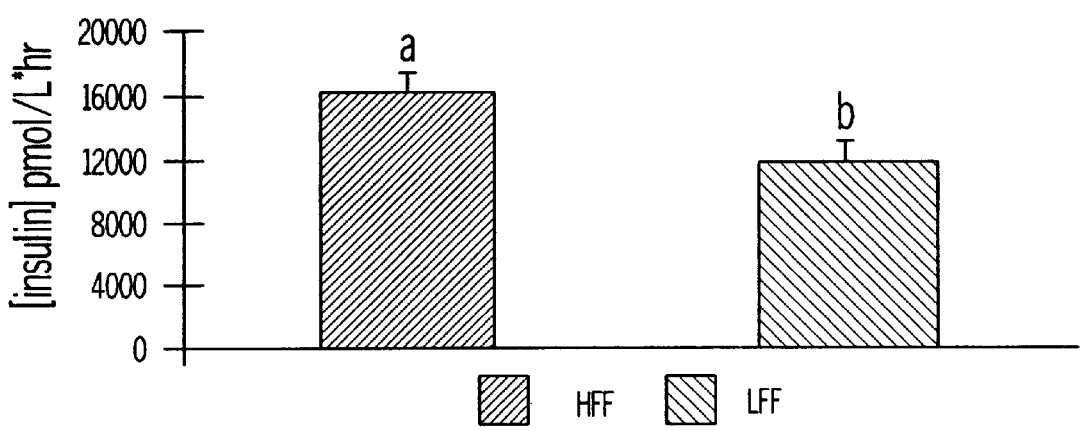
Figure 2C:
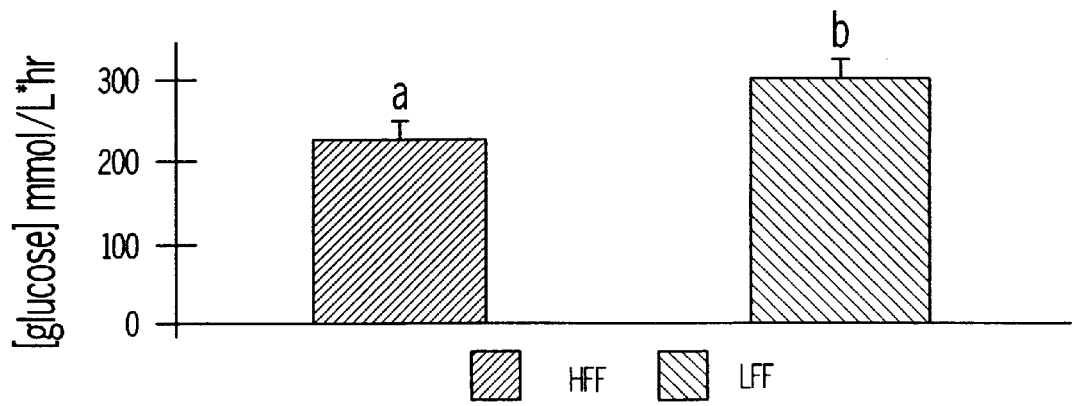

Effect of OGTT on plasma GLP-1, insulin and glucose. Plasma GLP-1 concentrations were increased at 30 and 90 min for dogs when fed the HFF vs the LFF diets (see, FIG. 1A). Insulin concentrations were increased at 90 min for dogs when fed the HFF vs the LFF diets (see, FIG. 1B). Dietary fiber type did not influence blood glucose concentrations at any time points during the OGTT (see, FIG. 1C). The incremental area under the curve was significantly higher for GLP-1 (see, FIG. 2A, 988±92 vs 648±92 pmol/L*h, p≦0.05) and insulin (see, FIG. 2B, 15781±1371 vs. 11209±1371 pmol/L*hr, p<0.05) when dogs were fed the HFF vs LFF diets. The area under the curve for glucose was significantly lower for dogs when fed the HFF vs LFF diets (219±22 mmol/L*hr vs 291±22 mmol/L*hr, p≦0.05, see, FIG. 2C). This demonstrates that the fermentable fiber diet increases the amount of GLP-1 and improves glucose homeostasis in the tested animals.

Figure 3:
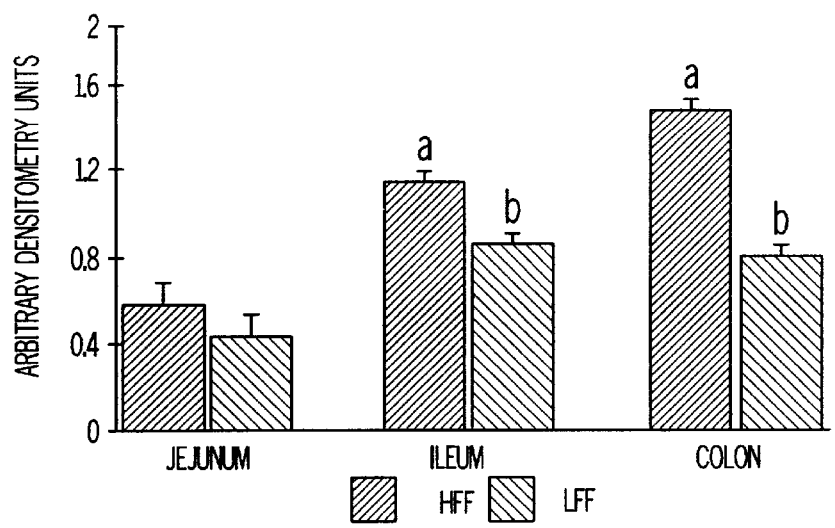
FIG. 3 is a chart showing the effect of fermentable fiber on intestinal proglucagon mRNA.

Effect of diet on intestinal proglucagon and GLP-1 concentration. Ingestion of HFF vs LFF diets resulted in greater proglucagon mRNA abundance in the ileum (1.13±0.04 vs. 0.83±0.04 densitometer units) and the colon (1.45±0.05 vs. 0.78±0.05 densitometer units) (see, FIG. 3). Proglucagon mRNA expression was not detected in the duodenum. GLP-1 concentrations, were significantly greater in mucosal scrapings from dogs fed the HFF vs LFF diets (41±4 pmol GLP-1/mg protein vs. 2535 4 pmol GLP-1/mg protein). This demonstrates again that the fermentable fiber diet increases GLP-1 concentrations in the tested animals.

Figure 4A:
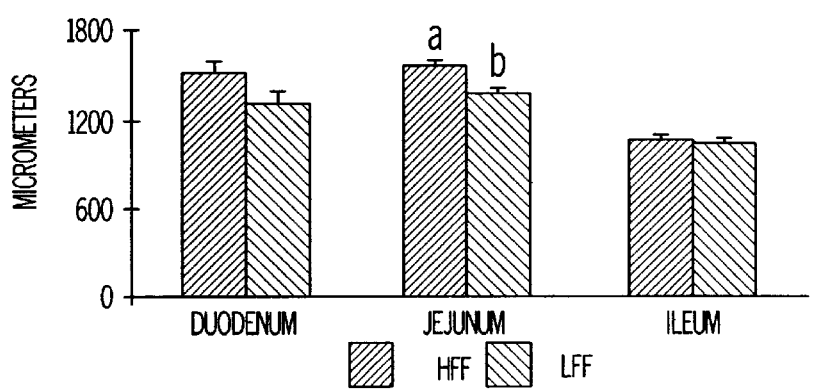
FIGS. 4A–4B are charts showing the effect of fermentable fiber on villi height (A) and crypt depth (B) in canine intestinal sections.
Figure 4B:
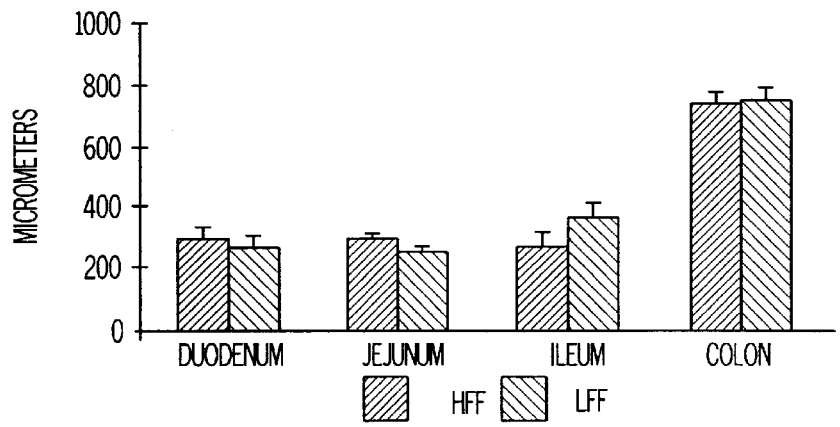

Histology. Dietary effects on intestinal villi heights and crypt depths are presented in FIG. 4. Duodenal villi heights tended to be higher in dogs fed the HFF diet compared to those fed the LFF diet (1505±83 vs 1294±83 μm, p=0.1) but there were no differences in duodenal crypt depths (289±28 vs 262±28 μm). Jejunal villi heights were significantly higher in dogs fed the HFF vs LFF diets (1517±43 vs 1343±43 μm, respectively) but no significant differences were found in crypt depths (277±19 vs 234±19 μm). Ileal villi heights and crypt depths were not significantly different between dogs fed the HFF vs. LFF diet (1035±45 vs 993±45 μm and 251±46 vs 357±46 μm, respectively). Colonic crypt depths were not significantly different (724±33 vs 727±33 μm) between dogs fed the HFF vs LFF diet, respectively.

Figure 5A:
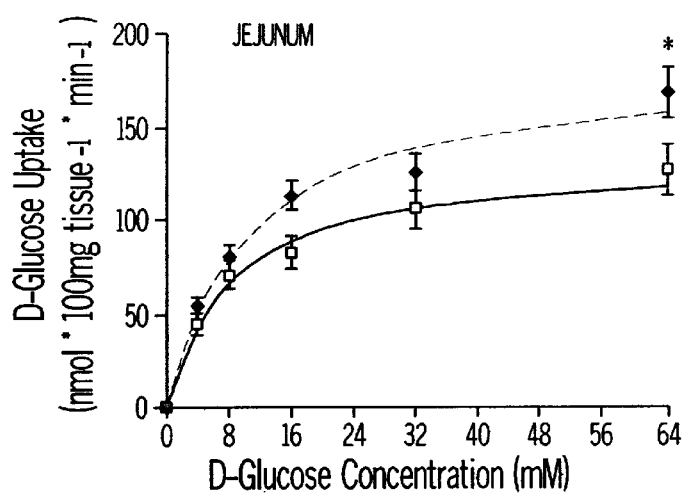
FIGS. 5A–5B illustrate the effect of fermentable fiber on the in vitro uptake of D-glucose into the jejunum (A) and ileum (B) of dogs.
Figure 5B:
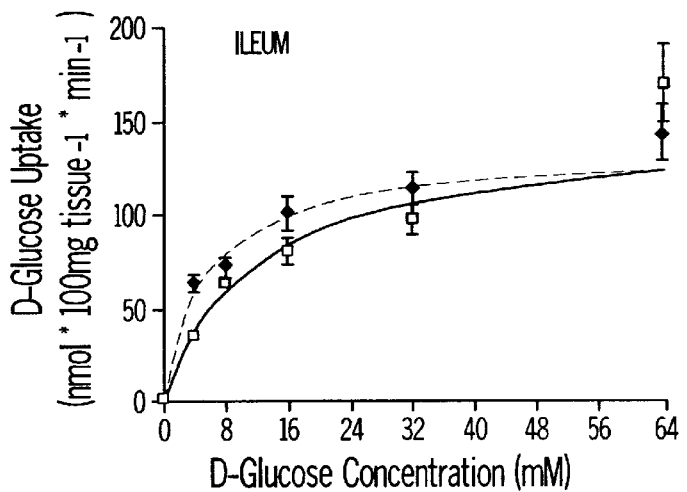

Nutrient uptake. The effect of dietary fiber fermentability on nutrient uptake is shown in Table 2. Consumption of HFF resulted in a significantly higher maximum glucose uptake capacity (Vmax) for D-glucose in the jejunum (see, FIG. 5). A significant diet effect was also noted in fatty acid-12 uptake in the jejunum, a measure of unstirred water layer resistance. The Michaelis affinity constant (Km) was not affected by diet. The estimation of paracellular D-glucose uptake, or the Kd for D-glucose as determined by extrapolation of L-glucose uptakes at 16 mM through the origin and normalizing to 1 mM, was not significantly affected by diet. Kd for D-fructose was not affected by diet.

Figure 6:
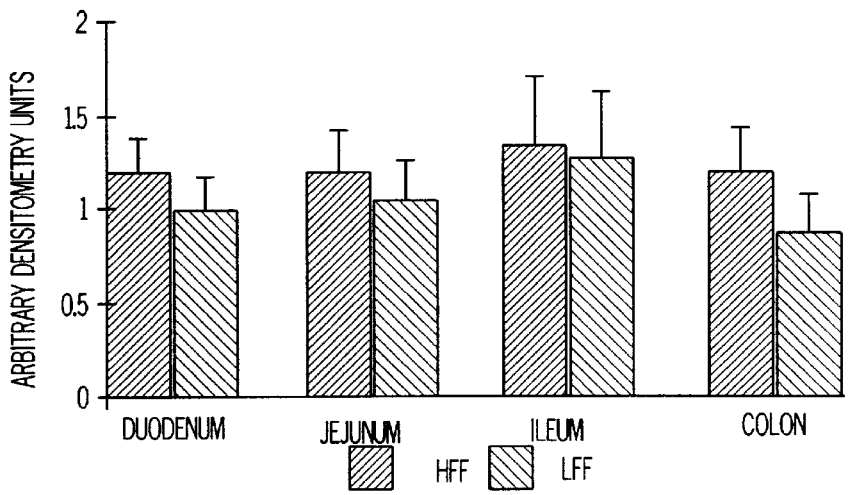
FIG. 6 is a chart of the effect of fermentable fiber on intestinal SGLT-1 transporter mRNA.
Figure 7A:
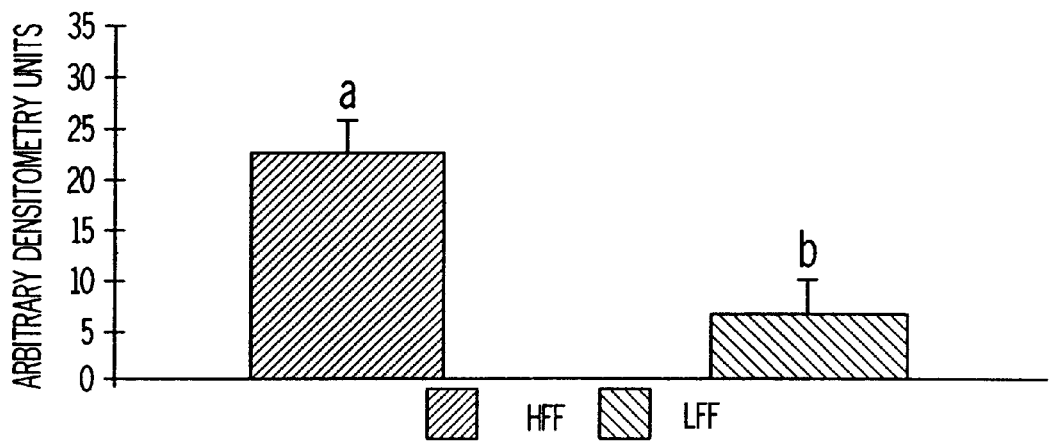
FIGS. 7A–7B illustrate the effect of fermentable fiber on jejunal (A) and ileal (B) SGLT-1 transporter abundance in dogs.
Figure 7B:
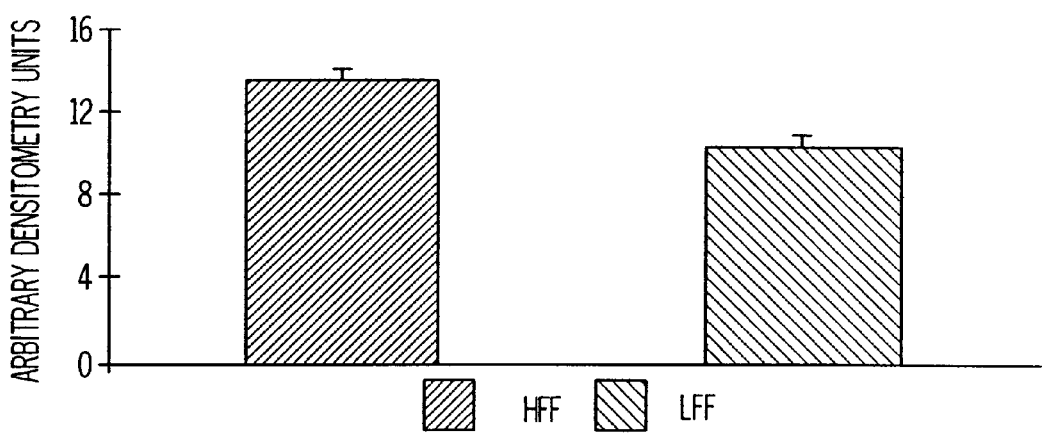
Figure 8A:
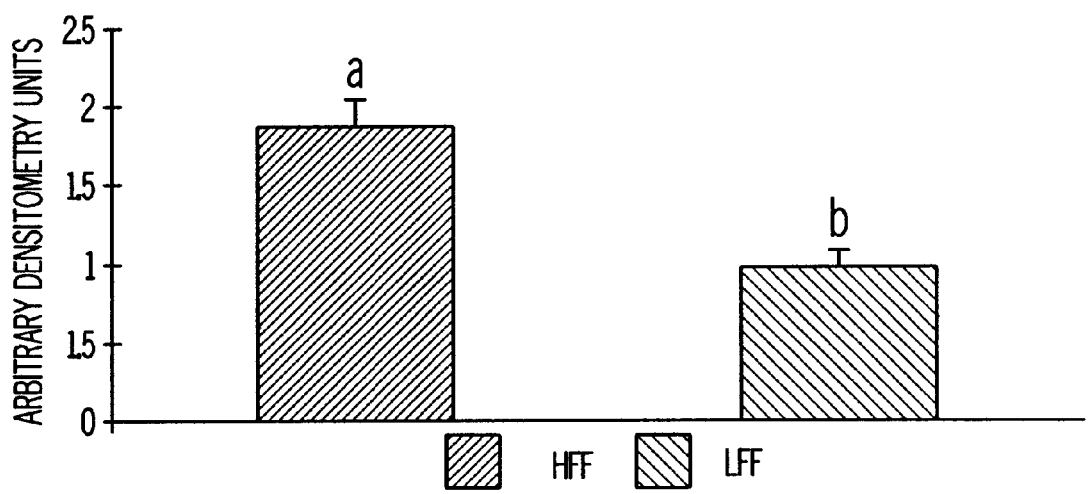
FIGS. 8A–8B illustrate the effect of fermentable fiber on intestinal GLUT2 transporter abundance in jejunum (A) and ileum (B) in dogs.
Figure 8B:
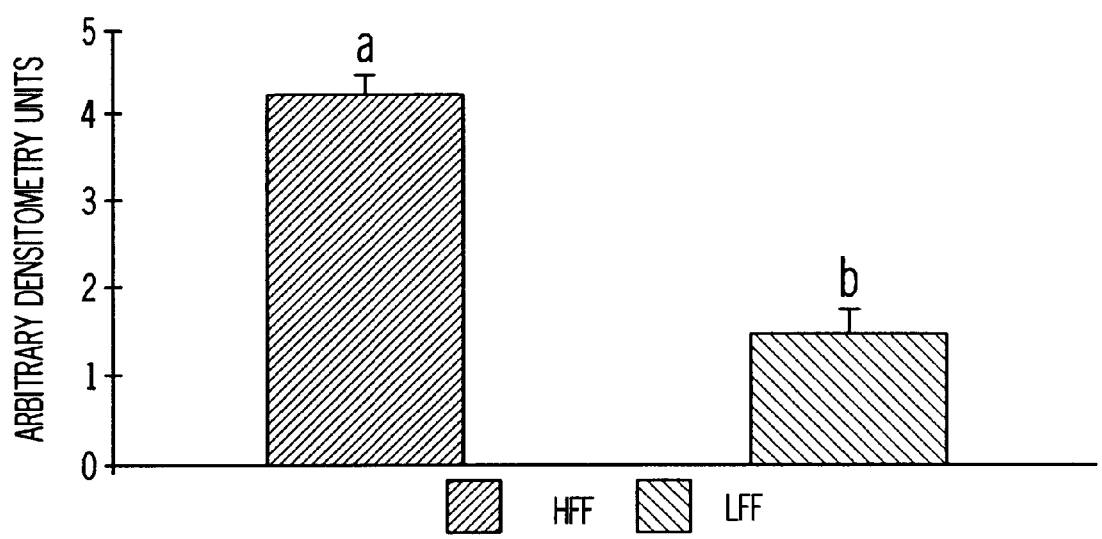

Glucose Transporters. Diet did not affect SGLT-1 mRNA in any of the intestinal segments measured (see, FIG. 6). The consumption of HFF vs. LFF diet was associated with higher jejunal SGLT-1 transporter protein abundance (22.2±3.7 vs 6.6±3.7 densitometer units). SGLT-1 transporter protein abundance tended to be higher in the ileum when HFF diet was consumed (13.4±0.7 vs 10.4±0.7 densitometer units, p=0.09, see, FIG. 7). Significant differences due to diet were seen in both jejunal and ileal GLUT2 transporter protein abundance (see, FIG. 8), showing an increase with consumption of HFF vs. LFF diet (1.9±0.2 vs. 0.9±0.1 densitometer units and 4.2±0.2 vs. 1.5±0.2 densitometer units, respectively).

TABLE 1

Composition of experimental diets

| Ingredient | Low-Fermentable Fiber (LFF) (g/kg diet as fed) | High Fermentable Fiber (HFF) (g/kg diet as fed) |
| --- | --- | --- |
| poultry by-product meal | 460 | 460 |
| poultry fat | 164 | 164 |
| fishmeal | 122 | 121 |
| pre-gelled cornstarch | 80 | 110 |
| Menhaden oil | 3 | 3 |
| dried whole egg | 40 | 40 |
| Chicken digest | 25 | 25 |
| vitamin premix | 3.2 | 3.2 |
| mineral premix | 2.4 | 2.4 |
| cellulose | 70 | — |
| beet pulp | — | 60 |
| gum arabic | — | 20 |
| fructooligosaccharides | — | 15 |
| Potassium chloride | 2.2 | 2.1 |
| Calcium chloride | 1.9 | 1.1 |
| Choline chloride | 1.1 | — |
| Sodium chloride | 0.3 | 0.3 |

TABLE 2

Intestinal transport rates in dogs fed highly-fermentable fiber (HFF) versus lowly-fermentable fiber (LFF) diets for 14 days

|  | Jejunum | | Ileum | |
| --- | --- | --- | --- | --- |
|  | HFF | LFF | HFF | LFF |
| D-glucose[1] | | | | |
| Vmax (nmol/mg tissue/min) | 182 ± 15[a] | 133 ± 13[b] | 132 ± 11 | 146 ± 15 |
| Km (mM) | 10.0 ± 1.9 | 8.0 ± 2.0 | 5.5 ± 1.2 | 12.7 ± 2.2 |
| L-glucose (nmol/mg tissue/min) | | | | |
| at 16 mM | 21.7 ± 1.2 | 21.5 ± 3.3 | 33.7 ± 5.3 | 27.8 ± 3.5 |
| at 1 mM | 1.4 ± 0.1 | 1.4 ± 0.2 | 2.1 ± 0.3 | 1.4 ± 0.2 |
| D-fructose (nmol/mg tissue/min) | | | | |
| Kd[2] | 1.96 | 1.61 | 2.43 | 2.28 |
| Fatty acid 12 uptake[3] (nmol/mg tissue/min) | 2.4 ± 0.2[a] | 1.7 ± 0.2[b] | 3.6 ± 0.5 | 4.2 ± 0.2 |

[1]Values are means ± SEM, n = 8 per diet. Differing letter superscripts indicate significant differences between diets within an intestinal site at $p < 0.05$.
[2]KD is the slope of the line describing the passive uptake of L-glucose, which also reflects the passive component of D-glucose uptake. Kd is equivalent to the uptake of 16 mM L-glucose normalized to 1 mM.
[3]Fatty acid 12 (lauric acid) uptake is a measure of unstirred water layer resistance.

EXAMPLE 2

Two groups of five adult beagles each with both sexes, were fed two diets that differed only in the source of fiber (see Table 3). Cellulose, which is minimally degraded during passage through the canine gastrointestinal tract (GIT), was added to the control diet (A) at a level of 3.6%. The second diet (B) contained beet pulp (4.2%) and fructooligosaccharides (FOS) (1%), which are fermented by the GIT bacteria of dogs. Chemical analyses showed both diets had 25.9% protein, 11.8% fat, with 6.2% moisture, 5.7% ash, 1.23% calcium, and 0.79% phosphorus. Diet B used a blend of beet pulp and FOS because differences in their rates of fiber fermentation by the intestinal bacteria of dogs. The products of bacterial metabolism of FOS, such as SCFA, should be available more proximally in the GIT compared to those from beet pulp, which is fermented slower. Furthermore, the two sources of fermentable fiber are designed to yield different concentrations and proportions of SCFA. The cellulose (Solka Floc) was obtained from Fiber and Sales Development Corporation (St. Louis, Mo.), the beet pulp from Michigan Sugar (Saginaw, Mich.), and FOS from Golden Technologies Company (Golden, Colo.).

TABLE 3

| Ingredient | Portion of Diet. wt % |
| --- | --- |
| corn grits | to 100 |
| chicken and chicken by-product meal | 23.4 |
| brewers rice | 15.9 |
| chicken fat | 4.2 |
| fiber source | a |
| fish meal | 3.3 |
| vitamin and mineral premix | 3.2 |
| chicken digest | 2.0 |
| dried egg product | 1.4 |
| fish oil | 0.75 |
| brewers dried yeast | 0.47 |
| flax | 0.28 |
| DL-methionine | 0.19 | a Diet A contained 3.6% cellulose and Diet B was prepared with 4.2% beet pulp and 1.0% FOS.

The dogs were housed in two groups in separate open kennels. The diets were fed for at least six weeks before surgery was performed. Immediately after surgery the small intestine was removed and the associated mesenteries were severed so the intestine could be straightened on a horizontal surface and length measured in a resting state. Three segments of 25–30 cm in length were removed and immediately placed in cold (2–4° C.) Ringers that had been aerated with a mixture of $O_2$ and $CO_2$ (95% and 5%). The first segment originated from 30 cm distal to the pylorus and was considered as proximal intestine. The second was taken from the mid point of the small intestine and was designated as mid intestine. The third segment, which started 30 cm from the ileocolonic junction and proceeded proximally, was considered to be representative of distal intestine.

From each of the three segments of small intestine a 10 cm length was used to determine wet weight per cm, circumference, and percentage of mucosa on a dry matter basis. Regional wet weights and nominal surface area (not accounting tor area amplification by villi and microvilli) were estimated as the products of regional weight per cm and circumference times regional length. Regional mucosal mass was estimated by multiplying percent mucosa times regional wet weight. Values for the entire intestine were calculated by summing the three regions.

A modification of the everted sleeve method (Karasov et al, J. Comp. Physiol. B 152:105–116 (1983)) was used to measure rates of nutrient uptake. Because adult beagles have a large diameter small intestine (>1 cm), it was not practical to use entire sleeves to measure nutrient absorption. Instead, pieces of tissue of about 0.5 $cm^2$ were secured by silk ligatures onto the sides and near the ends of 5 mm rods with the mucosa exposed. Preliminary validation studies showed that rates of uptake were comparable to those measured using intact sleeves of intestine (values differed<10% between mounting techniques). The tissues were kept in cold, aerated Ringers before, during, and after mounting onto the rods.

Measurements of uptake were performed at 37° C. and were started 45 min after removal of the intestine. Following the protocol of Puchal and Buddington, Am. J. Physiol., 262:G895–902 (1992), the incubation solutions consisted of Ringers with either glucose or proline. Accumulation of nutrient by the tissues was quantified by adding labeled L-proline ($^3$H) or D-glucose ($^{14}$C). Proline was selected as a representative amino acid since it has a "private" carrier (the imino acid transporter), whereas other amino acid carriers can transport several different classes of amino acids with varying affinities. Polyethylene glycol ($^{14}$C) was added to proline solutions to correct for proline associated with the adherent fluids and not actually absorbed. For glucose solutions, the passively absorbed isomer L-glucose ($^3$H) was added, allowing for simultaneous correction of D-glucose present in adherent fluids and passively absorbed independent of carriers. After the tissues were exposed to the nutrient solutions, they were removed from the rods (tissues exposed to glucose were first rinsed for 20 seconds in cold Ringers), and placed in tared vials. After wet weights were recorded, the tissues were solubilized, scintillant added, and associated radioactivity was measured by liquid scintillation counting. Rates of glucose and proline uptake were calculated and expressed as functions of tissue weights.

The regional distribution of uptake was determined by incubating tissues from each segment in solutions containing 50 mmol/L solutions of glucose or proline. Preliminary studies showed that this concentration is sufficiently high that it saturates the carriers and yields maximal rates of absorption. The maximum capacity of the entire length of small intestine to absorb glucose and proline was estimated by summing the products of regional rates of uptake times regional wet weights.

Kinetics of uptake were defined in the proximal intestine for glucose and the mid intestine for proline. This was accomplished by exposing tissues to Ringers with 0.04, 0.2, 1, 5, 25, and 50 mmol/L of unlabeled glucose and proline. Resulting uptake values were examined by non-linear regression analysis to calculate maximal rates of uptake (Vmax) and apparent affinity constants (Km). For analysis of proline data, a passive permeation coefficient was included to account for proline absorbed passively and independent of carriers.

Values presented in tables and figures are means and standard errors. ANOVA was used to search tor effects of diet and region on dimensions and rates of glucose and proline absorption. When a significant regional effect was detected, Duncan's test was used to identify specific differences. Analyses of the data were performed using the Statistical Analysis System (SAS, Version 6.11, Cary, N.C.), with p<0.05 accepted as the critical level of significance.

Body weights did not differ between dogs fed the two diets. However, dogs fed the diet with the blend of beet pulp and FOS as sources of fermentable fiber (Diet B) had intestines that were 22% longer than those fed the diet with non fermentable fiber (Diet A) (p=0.09; see Table 4). Circumference declined from proximal to distal (p<0.05). Although values did not differ significantly between treatments in any region, when all three regions were combined, dogs fed diet B with fermentable fiber had 28% more total intestinal surface area available for absorption.

Wet weight per cm declined from proximal to distal in both groups, with significant differences between all regions (p<0.05). Intestines of dogs fed fermentable fiber had a higher average wet weight per cm (1.17 vs 1.04; p<0.05), due mainly to the greater mass of the proximal intestine (p<0.05). The wet weight per cm for mid and distal regions did not differ significantly between treatments. The higher total intestinal wet weight of dogs fed fermentable fiber is therefore due to a combination of having longer intestines with more weight per cm in the proximal intestine. Dry weight per cm also declined from proximal to distal (p<0.05), but did not differ between treatments in any region, indicating the heavier proximal intestine per cm of dogs fed fermentable fiber is partly due to higher water content. Even so, dogs fed fermentable fiber had more total intestinal dry mass.

The percentage of mucosa did not differ between regions (p>0.50) or between treatments in any region (p's>0.70). The averages for all three regions were, respectively, 39%±0.02 and 39% ±0.03 for dogs fed the diets with and without fermentable fiber. Because of greater total intestinal weight, total intestinal mucosa mass was greater in dogs fed the diet with fermentable fiber.

TABLE 4

| Parameter | Diet A | Diet B |
| --- | --- | --- |
| Body weight (kg) | 10.18 ± 1.05 | 10.18 ± 0.47 |
| Intestinal length (cm) | 306 ± 26* | 372 ± 23 |
| Intestinal surface area (cm$^2$) | 1240 ± 95* | 1582 ± 96 |
| Intestinal wet weight (g) | 318 ± 23* | 430 ± 17 |
| Intestinal dry weight (g) | 60.9 ± 3.1* | 77.9 ± 5.7 |
| % Mucosa | 39 ± 3 | 39 ± 2 |

*Asterisk indicates significant effects based on diet.

Values tor glucose uptake represent carrier mediated transport. Rates of uptake at the saturating concentration of 50 mmol/L were highest in the proximal intestine (FIG. 9, p<0.05 for region effects), but were not significantly higher in dogs fed the diet with fermentable fiber (p>0.20 for treatment effects). Values for mid and distal intestine did not differ significantly from each other or between treatments.

Figure 10:
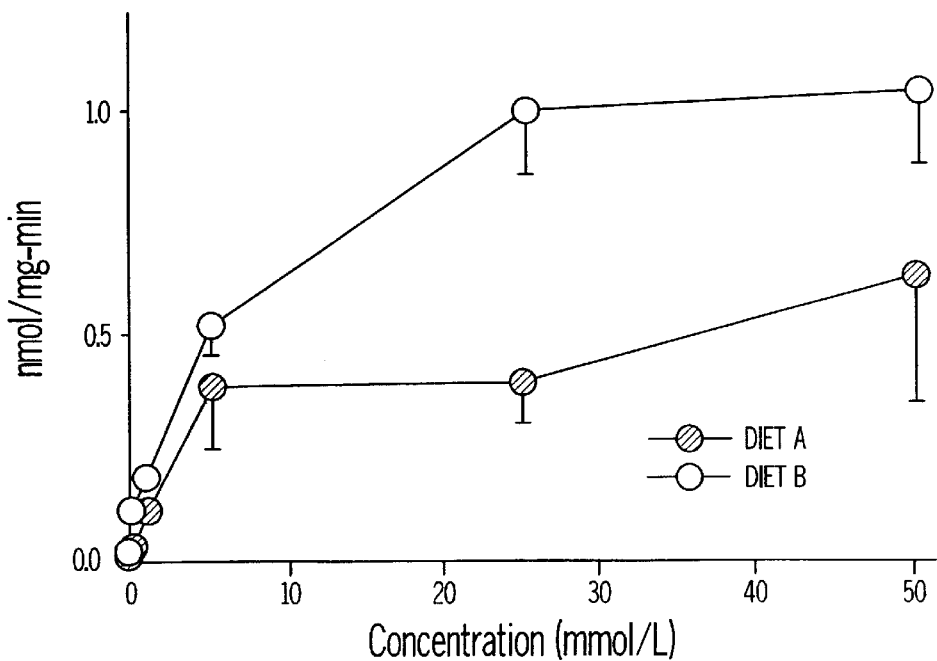
FIG. 10 illustrates the uptake by the proximal intestine as a function of glucose concentration.

Kinetic analysis of uptake by proximal intestine as a function of glucose concentration (FIG. 10) showed saturable uptake for dogs from both treatments.

Although values for uptake at 50 mmol/L did not differ significantly between treatments, the kinetic analysis showed that dogs fed the diet with fermentable fiber had higher maximum rates of uptake (1.21±0.11 nmol/mg-min vs 0.60± 0.13, p<0.05). Apparent affinity constants did not differ between treatments (6.2±2.1 vs 3.9±3.3) implying only one transporter type was present.

Figure 9:
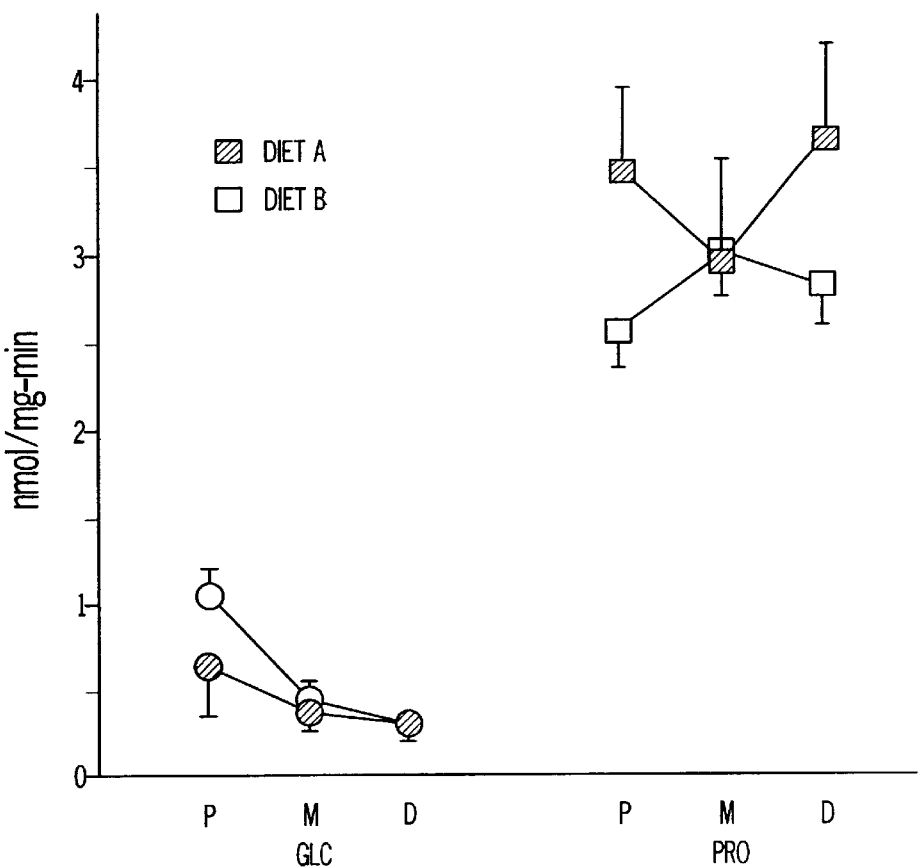
FIG. 9 is a graph of the rates of glucose (GLC) and proline (PRO) uptake in the proximal (P), mid (M), and distal (D) intestine.

Values for rates of proline uptake represent the sum of carrier-mediated uptake and passive, carrier-independent absorption. Values at 50 mmol/L did not differ between treatments or region (FIG. 9).

Figure 11:
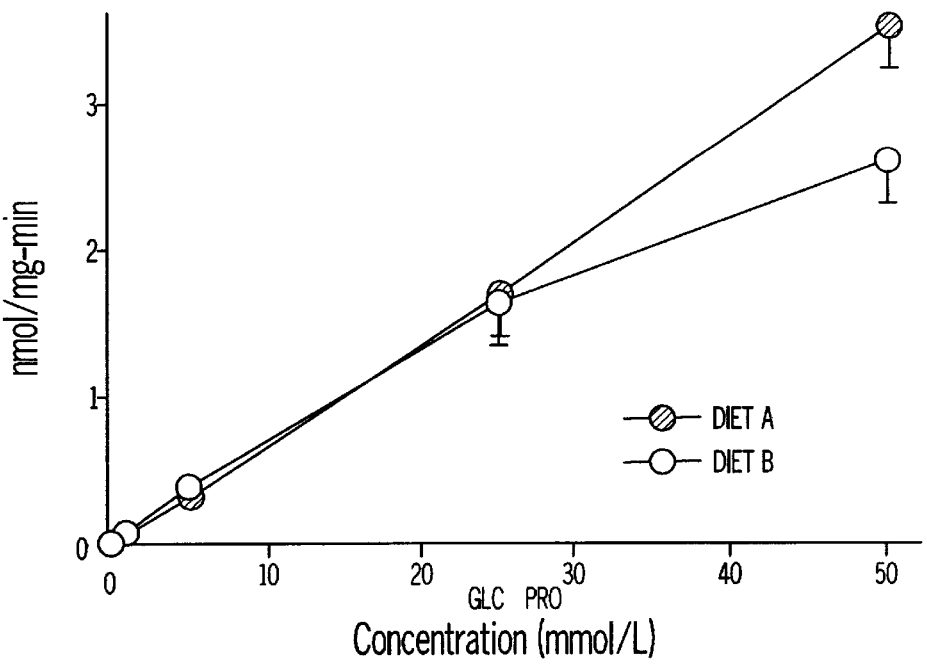
FIG. 11 illustrates the uptake by the proximal intestine as a function of proline concentration.

Proline uptake by dogs fed the diet with cellulose (Diet A) increased monotonically with proline concentration (FIG. 11), did not show any evidence of saturation kinetics typical of carrier-mediated processes, and were best fit by a linear relationship. As an additional indicator, ratios for the accumulation of tracer proline were calculated at 0.04 mmol/L relative to 50 mmol/L. If carriers are present in limited numbers, the labeled and unlabeled proline would have to compete for carrier sites. This would result in ratios would that would exceed 1.0 because of the reciprocal relationship between accumulation of tracer and nutrient concentration. Ratios for dogs fed the diet with cellulose averaged 0.96±0.11 indicating a lack of competition. These findings, in conjunction with those from the kinetic analysis, indicate that passive influx represented nearly 100% of total proline absorption and that there were few transporters present or functioning.

In contrast, when dogs were fed the diet with fermentable fiber (Diet B), the relationship between rates of uptake and proline concentration deviated from linearity and was best fit by an equation that included a saturable process and passive influx. This was corroborated by tracer accumulation ratios that averaged 1.21±0.15. This value does not differ significantly from 1.0 and is markedly less than ratios for glucose (9.13±1.36 and 4.58±0.80 tor dogs fed diets with and without fermentable fibers, respectively, p<0.05 for comparisons with 1.0 and between treatments). However, it is suggestive that more carriers for proline are present in the mid intestine when dogs are fed a diet with fermentable fiber. Even so, passive influx at 50 mmol/L proline still contributes over 90% of total influx.

The affinity constant for proline uptake by intact tissues from other vertebrates ranges from about 1 to 5 mmol/L. If the imino transporter of dogs is similar to those known for other mammals, then all of the carriers should be saturated at the concentration of 25 mmol/L. Therefore, any increase in proline absorption between 25 and 50 mmol/L should reflect passive, carrier-independent influx. When the slopes of the lines between 25 and 50 mmol/L were compared, no difference between dogs fed diets A (0.074±0.022 nmol/mg-min-mmol/L) and B (0.054±0.011, p>0.20) could be detected.

Figure 12:
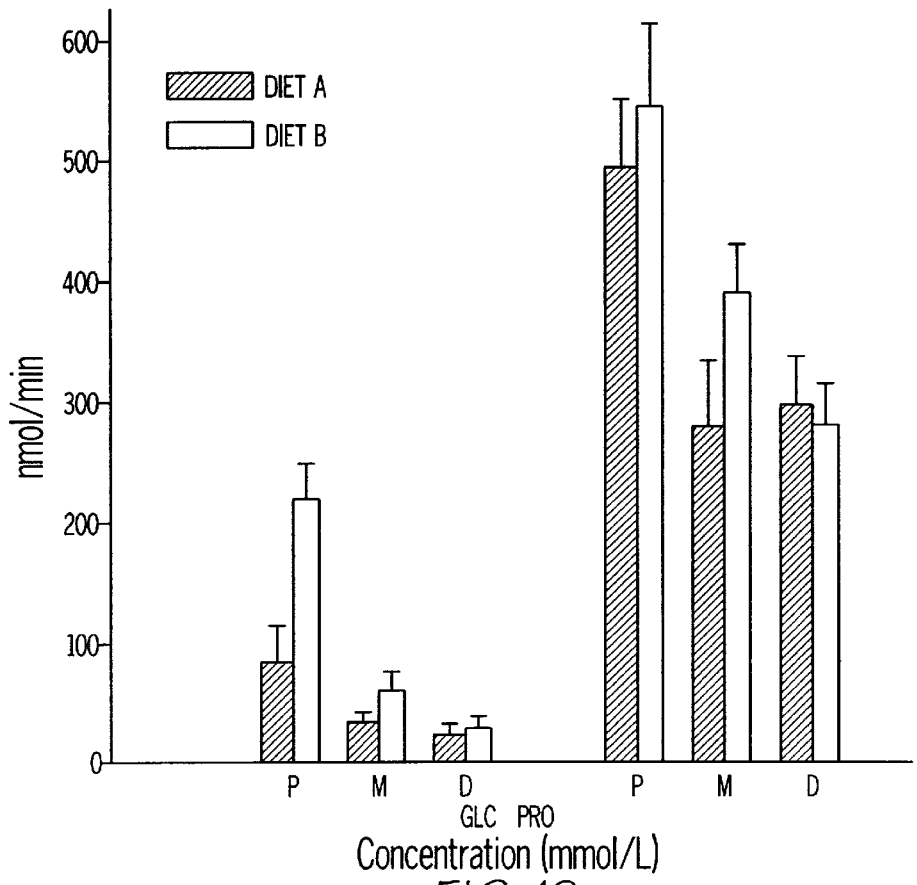
FIG. 12 is a chart illustrating the intestinal capacities of dogs to absorb glucose (GLC) and proline (PRO) in the proximal (P), mid (M), and distal (D) intestine.

When rates of uptake were integrated with regional wet weights, dogs fed the diet with fermentable fiber had higher total intestinal capacities to absorb glucose (271±42 μmol/min vs 139±37; p<0.05). This was mainly caused by higher values in proximal intestine; values for mid and distal intestine did differ between treatments (FIG. 12). Treatment effects were not detected for proline uptake capacities in any region (FIG. 12), or for the entire length of small intestine (Diet A=1246±155, Diet B=1031±124; p>0.40).

This experiment demonstrates that the intestinal-structure and functions of dogs are altered by the types of fibers present in the diet. The results demonstrate longer, heavier intestines with more surface area and mucosa result when dogs are fed a diet with fibers that can be readily fermented by the GIT bacteria. The responses were more pronounced in the proximal intestine, as evident from the differences in proximal weight and mucosal mass between dogs fed the two diets. The lack of difference in the percent of mucosa in proximal intestine, or any other region of the intestine (p>0.9) indicates there was an increase in all tissue layers. However, because of greater mass of the proximal region, dogs fed the diet with fermentable fiber had more mucosa in the proximal region as well as the entire length of small intestine. The implication is that dogs fed a diet with fermentable fibers have more intestine to hydrolyze and absorb dietary inputs. The results also indicate that including fermentable fibers in canine diets provide benefits to healthy dogs that are in addition to the increases in the beneficial GIT bacteria.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for altering the function and composition of the gastrointestinal tract (GIT) of a companion animal to improve glucose metabolism comprising the steps of:
   feeding said companion animal a diet containing from about 1 to 11 weight percent of supplemental total dietary fiber, said supplemental total dietary fiber consisting essentially of a blend of beet pulp, fructooligosaccharides, and either gum talha or gum arabic wherein the ratio of said beet pulp to gum arabic or gum talha to fructooligosaccharides is about 6:2:1.5; and
   maintaining said animal on said diet for a sufficient period of time to allow said composition to ferment in the GIT of said animal.

2. The process of claim 1 wherein said composition contains from 2 to 10 weight percent of supplemental total dietary fiber of said blend.

3. The process of claim 1 wherein said composition contains from 3 to 9 weight percent of supplemental total dietary fiber of said blend.

4. The process of claim 1 wherein said composition contains from 4 to 7 weight percent of supplemental total dietary fiber of said blend.

5. The process of claim 1 wherein said animal is a dog.

6. A process for altering the function and composition of the gastrointestinal tract (GIT) of a companion animal to improve glucose metabolism comprising the steps of:
   feeding said companion animal a diet containing from about 1 to 11 weight percent of supplemental total dietary fiber, said supplemental total dietary fiber consisting essentially of a blend of beet pulp, fructooligosaccharides, and either gum talha or gum arabic wherein the ratio of said beet pulp to said fructooligosaccharides in said blend is between about 3:1 to about 6:1, and
   maintaining said animal on said diet for a sufficient period of time to allow said composition to ferment in the GIT of said animal.

7. The process of claim 6 wherein the ratio of said beet pulp to said fructooligosaccharides in said blend is about 4:1.

8. A process for increasing the secretion of glucagon-like peptide-1 (GLP-1) in the gastrointestinal tract (GIT) of a companion animal to improve glucose metabolism and satiety in said animal comprising the steps of:
   feeding said companion animal a diet containing from about 1 to 11 weight percent of supplemental total dietary fiber, said supplemental total dietary fiber consisting essentially of a blend of beet pulp fructooligosaccharides, and either gum talha or gum arabic wherein the ratio of said beet pulp to said fructooligosaccharides in said blend is between about 3:1 to about 6:1, and
   maintaining said animal on said diet for a sufficient period of time to allow said composition to ferment in the GIT of said animal to increase the secretion of GLP-1 in the gastrointestinal tract of said animal.

9. The process of claim 8 wherein the ratio of said beet pulp to gum arabic or gum talha to fructooligosaccharides is about 6:2:1.5.

10. A process for improving nutrient absorption in the gastrointestinal tract (GIT) of a companion animal comprising the steps of:
    feeding said companion animal a diet containing from about 1 to 11 weight percent of supplemental total dietary fiber, said supplemental total dietary fiber consisting essentially of a blend of beet pulp, fructooligosaccharides, and either gum talha or gum arabic wherein the ratio of said beet pulp to said fructooligosaccharides in said blend is between about 3:1 to about 6:1, and
    maintaining said animal on said diet for a sufficient period of time to allow said composition to ferment in the GIT of said animal to increase the transport of D-glucose and lauric acid in the gastrointestinal tract of said animal.

11. The process of claim 10 wherein the ratio of said beet pulp to gum arabic or gum talha to fructooligosaccharides is about 6:2:1.5.

12. A process for treating a companion animal suffering from exocrine pancreatic insufficiency (EPI) comprising the steps of:

feeding said companion animal a diet containing from about 1 to 11 weight percent of supplemental total dietary fiber, said supplemental total dietary fiber consisting essentially of a blend of beet pulp, fructooligosaccharides, and either gum talha or gum arabic wherein the ratio of said beet pulp to said fructooligosaccharides in said blend is between about 3:1 to about 6:1, and maintaining said animal on said diet for a sufficient period of time to allow said composition to ferment in the GIT of said animal to increase nutrient absorption and the transport of D-glucose and lauric acid in the gastrointestinal tract of said animal.

13. The process of claim 12 wherein the ratio of said beet pulp to gum arabic or gum talha to fructooligosaccharides is about 6:2:1.5.

* * * * *